United States Patent [19]

Goddard

[11] 3,987,057

[45] Oct. 19, 1976

[54] HERBICIDAL 2-(SUBSTITUTED ARYL)-3A,4,5,6,7,7A-HEXAHYDRO-1H-ISOINDOLE-1,3(2H)-DIONES

[75] Inventor: Steven Jerome Goddard, West Grove, Pa.

[73] Assignee: E. I. Du Pont de Nemours and Company, Wilmington, Del.

[22] Filed: Jan. 30, 1975

[21] Appl. No.: 545,604

[52] U.S. Cl. .............................. 260/326 HL; 71/96
[51] Int. Cl.² ........................................ C07D 209/48
[58] Field of Search............................ 260/326 HL

[56] References Cited
UNITED STATES PATENTS

| | | | |
|---|---|---|---|
| 2,900,243 | 8/1959 | Lewis ............................ | 260/326 HL |
| 3,654,302 | 4/1972 | Schwartz et al. ............. | 260/326 HL |
| 3,745,170 | 7/1973 | Fujinami et al. ............. | 260/326 HL |

FOREIGN PATENTS OR APPLICATIONS

| | | | |
|---|---|---|---|
| 2,119,703 | 7/1972 | France........................... | 260/326 HL |

Primary Examiner—Lewis Gotts
Assistant Examiner—S. P. Williams

[57] ABSTRACT

This invention relates to herbicidal 2-(substituted aryl-)-3a,4,5,6,7,7a-hexahydro-1H-isoindole-1,3(2H)-diones. These compounds may be used for selective weed control for certain crops or for total vegetation control. In particular, the compounds may be utilized as rice herbicides and have the formula

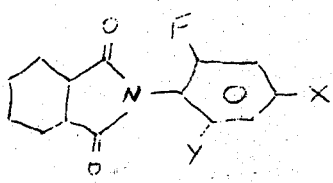

wherein X is Cl, Br or F, and Y is H or F, provided that when Y is F, X is F.

3 Claims, No Drawings

HERBICIDAL 2-(SUBSTITUTED ARYL)-3A,4,5,6,7,7A-HEXAHYDRO-1H-ISOINDOLE-1,3(2H)-DIONES

BACKGROUND OF THE INVENTION

A number of isoindole-type compounds are known in the prior art. Recently, in German Offenlegungsschrift 2,165,651 a group of isoindole-1,3-diones which are useful as herbicides was disclosed. The general formula for the isoindole-1,3-diones disclosed in the Offenlegungsschrift is as follows:

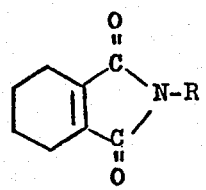

wherein R may be an aryl, aralkyl or benzyl optionally substituted with 1 to 5 halogen atoms; hydroxy, nitro, cyano, thiocyano, carboxy, halogenated alkyl, or alkyl, or alkoxy, lower alkylthio, phenyl groupings and a group having the configuration -O-CH$_2$A may also be substituted therein, wherein A is a phenyl or a naphthyl group, wherein the phenyl group may have one or more substitutions therein, such as halogen atoms, nitro groupings, lower alkyl groupings or lower alkoxy groupings.

Typical of the compounds disclosed in the Offenlegungsschrift is the compound of Example 1:

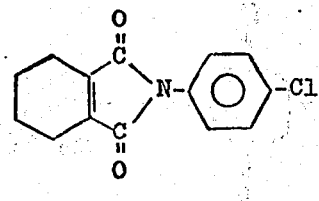

In U.S. Pat. No. 2,900,243 there is a disclosure of herbicidal activity for 2-(4-halophenyl)-3a,4,5,6,7,7a-hexahydro-1H-isoindole-1,3(2H)-diones; the phenyl and 2-chlorophenyl analogs are described as being inactive as herbicides at application rates of 25 lbs/acre.

None of the compounds which are disclosed above have demonstrated high herbicidal activity in conjunction with virtually no damage to the crop which is to be protected. That is to say, if any of the compounds was an effective herbicide it tended also to damage crops. The compounds of this invention are effective herbicides which may be used for selective weed control in certain crops, particularly rice.

According to the instant invention, compounds have been discovered which have high herbicidal activity with selectivity for certain crops.

SUMMARY OF THE INVENTION

This invention relates to novel compounds of the following formula and their use as herbicides:

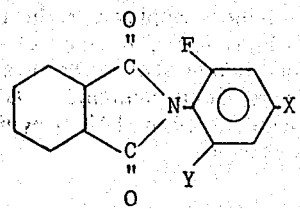

Formula I wherein X is Cl, Br or F, and Y is H or F, provided that when Y is F, X is F.

This invention also includes herbicidal compositions containing the above compounds as active ingredients and methods of controlling undesirable vegetation by applying the compounds and/or compositions to the locus of such undesired vegetation.

DESCRIPTION OF THE INVENTION

The 2-(substituted aryl)-3a,4,5,6,7,7a-hexyhydro-1H-isoindoles-1,3(2H)-diones of this invention are prepared by reaction of an appropriately substituted aniline with cyclohexane-1,2-dicarboxylic anhydride as shown in the following reaction:

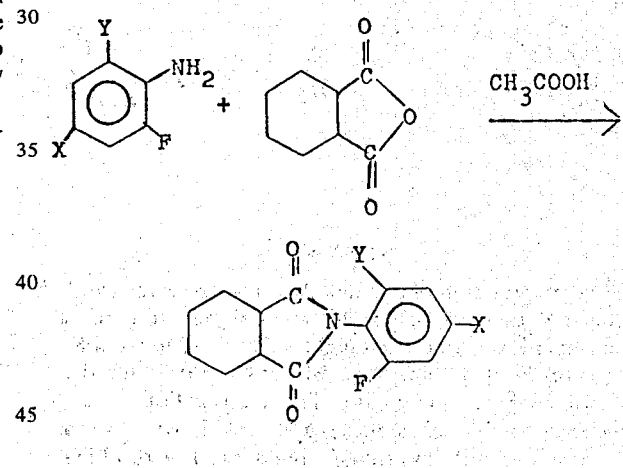

Formula I wherein
X is Cl, Br or F, and Y is H or F, provided that when Y is F, X is F.

The di- or trihaloaniline and cyclohexane-1,2-dicarboxylic anhydride are refluxed together in glacial acetic acid at temperatures of 115°–120° C and atmospheric pressure for several hours (e.g., more than 5). The di- or trihalophenyl-3a,4,5,6,7,7a-hexahydro-1H-isoindole-1,3(2H)-dione is isolated by precipitation with water followed by filtration.

The following are compounds prepared by the process described above:

2-(4-chloro-2-fluorophenyl)-3a,4,5,6,7,7a-hexahydro-1H-isoindole-1,3(2H)-dione m.p. 94°–95.5° C.
2-(4-bromo-2-fluorophenyl)-3a,4,5,6,7,7a-hexahydro-1H-isoindole-1,3(2H)-dione m.p. 90°–92° C.
2-(2,4-difluorophenyl)-3a,4,5,6,7,7a-hexahydro-1H-isoindole-1,3(2H)-dione m.p. 117°–123° C.
2-(2,4,6-trifluorophenyl)-3a,4,5,6,7,7a-hexahydro-1H-isoindole-1,3(2H)-dione m.p. 129°–131° C.

Certain of the anilines employed in the synthesis of the compounds of this invention are novel. 4-chloro-2-fluoroaniline, for example, can be prepared from 2'-fluoroacetanilide [G. Schiemann and H. G. Baumgarten, Chem. Berichte 70, 1416 (1937)] by the reaction sequences shown below.

2-Fluoro-4-bromoaniline can be prepared by bromination of 2-fluoroaniline (prepared in Chem. Berichte, 70, 1416 (1937)) with N-bromosuccinimide as shown in the following equation.

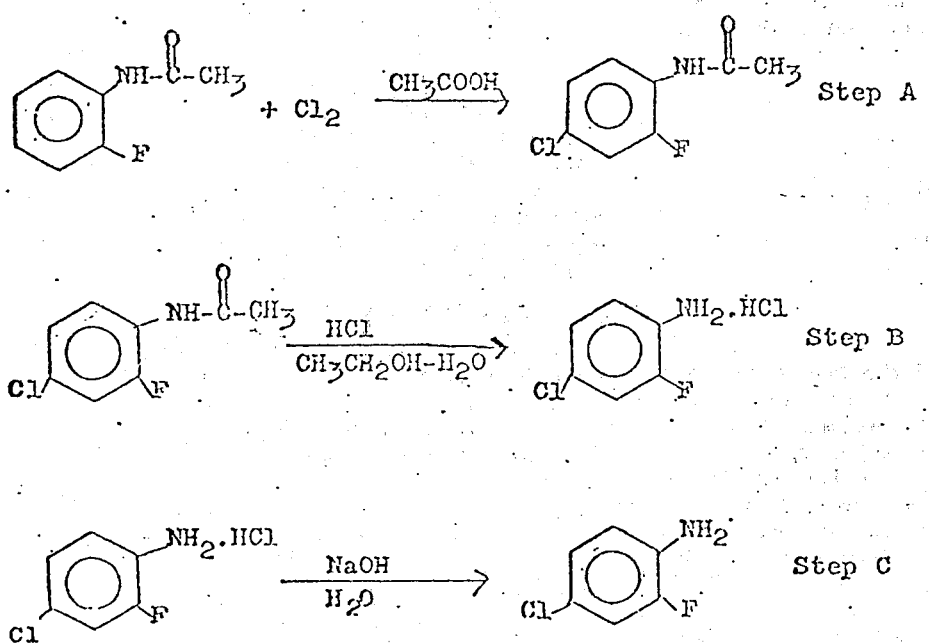

STEP A

The chlorination of acetanilides in acetic acid is well known to those skilled in the art, and may be carried out under the conditions taught in W. W. Reed and K. J. P. Orton, J. Chem. Soc., 91, 1543 (1907) for the chlorination of acetanilide. The chlorination of 2'-fluoroacetanilide takes place at 25°–30° C over several hours (e.g. 5) at atmospheric pressure. The resulting product is 4'-chloro-2'-fluoroacetanilide.

STEP B

The chlorofluoroacetanilide is refluxed in a mixture of a lower alcohol (50%) (e.g. ethanol) and concentrated hydrochloric acid (50%) for several hours (e.g. 5 or more) at 70°–90° C and atmospheric pressure. The solvent mixture is removed at a reduced pressure of 100 to 300 mm Hg. and at a temperature of 20°–50° C to leave a residue of the hydrochloride salt of 4-chloro-2-fluoroaniline.

STEP C

After basification of an aqueous solution of the hydrochloride salt of 4-chloro-2-fluoroaniline with an alkali metal hydroxide solution, such as 50% sodium hydroxide at ambient conditions, the free 4-chloro-2-fluoroaniline is extracted into a suitable water-immiscible organic solvent such as ethyl ether or methylene chloride. The crude 4-chloro-2-fluoroaniline is isolated by removal of the organic solvent under reduced pressure of 100 to 300 Hg. at 20°–50° C.

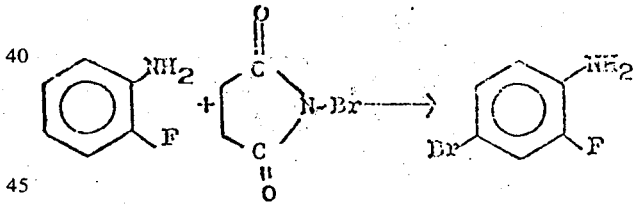

The bromination of anilines using N-bromosuccinimide in an inert organic solvent such as methylene chloride is well known to those skilled in the art, e.g., J. B. Wommack et al., J. Het. Chem., 6, 243 (1969). The bromination of 2-fluoroaniline is an exothermic reaction that takes place at 0° C over several hours, e.g. 5 or more. The resulting reaction mixture is washed with water several times and dried with an appropriate drying agent such as anhydrous sodium sulfate. The 4-bromo-2-fluoroaniline is recovered by removal of the organic solvent under reduced pressure of 100 to 300 mm Hg. at 20°–50° C.

2,4,6-Trifluoroaniline is prepared by reduction of 1,3,5-trifluoro-2-nitrobenzene [V. I. Siele and H. J. Matsuguma, U.S. Dept. Com., Office Serv., P B Rept. 145, 510, p. 1 (1960) or Chem. Abst. 56 15394c (1962)] using the procedures described by G. Schiemann and M. Seyhan, Chem. Berichte, 70, 2396 (1937).

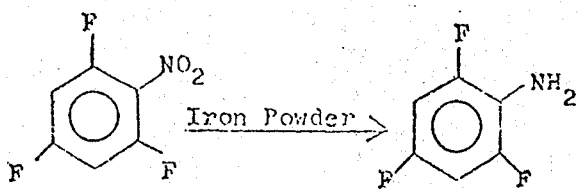

2,4-Difluoroaniline is known to the art and can be prepared by the procedure described in G. Schiemann and M. Seyhan, Chem. Berichte, 70, 2396 (1937).

The following examples further illustrate the method for synthesis of compounds of this invention. All parts are by weight and all temperatures in degrees centigrade unless otherwise indicated.

EXAMPLE 1

Preparation of
2-(4-chloro-2-fluorophenyl)-3a,4,5,6,7,7a-hexahydro-1H-isoindole-1,3(2H)-dione Seventy-one parts of liquid chlorine were added to a solution of 140 parts of 2'-fluoroacetanilide in 500 parts glacial acetic acid, during 1 hour, at 25°–27° C, with icewater cooling. While stirring for 4 hours at 25°–27° C, 4'-chloro-2'-fluoroacetanilide precipitated. After collecting the product by filtration, the filtrate was poured over 2,000 parts of ice. The resulting second portion of precipitated product was collected by filtration, combined with the first portion and recrystallized from 700 parts of methanol at −45° C to yield 119 parts of 4'-chloro-2'-fluoroacetanilide as white crystals melting at 152°–155° C.

A mixture of 119 parts of 4'-chloro-2'-fluoroacetanilide in 475 parts of ethanol and 200 parts of 37% hydrochloric acid was refluxed for 17 hours and the solvent removed under a reduced pressure of 300 mm.Hg. to yield the moist, solid hydrochloride salt of 4-chloro-2-fluoroaniline.

The moist, solid hydrochloride salt of 4-chloro-2-fluoroaniline was cooled to 10° C in an ice-acetone bath and 50% aqueous sodium hydroxide was added dropwise, with stirring, until pH 11 was obtained. The resulting two-phase mixture was extracted four times; 500 parts of methylene chloride were used for each extraction. The combined organic extracts were dried with anhydrous sodium sulfate and the solvent removed under reduced pressure of 300 mm Hg. to leave 89 parts of light brown, oily 4-chloro-2-fluoroaniline, $n_D^{25}$ = 1.5541.

9.44 Parts of 4-chloro-2-fluoroaniline were then added to a solution of 10 parts of cyclohexane-1,2-dicarboxylic anhydride in 75 parts of glacial acetic acid. After refluxing for 6 hours, the reaction mixture was poured into 200 parts of ice. The resulting crystals were filtered and recrystallized from 70 parts of methanol at −40° C to yield 12.4 parts of white crystals of 2-(4-chloro-2-fluorophenyl)-3a,4,5,6,7,7a-hexahydro-1H-isoindole-1,3(2H)dione melting at 94°–95.5° C.

EXAMPLE 2

Preparation of
2-(4-bromo-2-fluorophenyl)-3a,4,5,6,7,7a-hexahydro-1H-isoindole-1,3(2H)-dione 160 Parts of solid N-bromosuccinimide were added in portions over a 2 hour period to a solution of 100 parts of 2-fluoroaniline in 400 parts of methylene chloride cooled to 0° C. After stirring for 20 minutes, the dark red mixture was washed four times; 200 parts of cold water were used for each washing. The red organic phase was dried with anhydrous sodium sulfate and evaporated under 300 mm.Hg. to 164 parts of brown, oily 4-bromo-2-fluoroaniline, $n_D^{25}$: 1,5885.

11.4 Parts of 4-bromo-2-fluoroaniline were added to a solution of 10 parts of cyclohexane-1,2-dicarboxylic anhydride in 100 parts of glacial acetic acid and the mixture was stirred for 2 hours. The mixture was refluxed for 20 hours and then poured into 200 parts of ice. The resulting purple crystals were filtered and recrystallized from 70 parts of methanol at −40° C to yield 7.6 parts of lavender crystals of 2-(4-bromo-2-fluorophenyl)-3a,4,5,6,7,7a-hexahydro-1H-isoindole-1,3(2H)-dione melting at 90°–92° C.

EXAMPLE 3

Preparation of
2-(2,4-difluorophenyl)-3a,4,5,6,7,7a-hexahydro-1H-isoindole-1,3(2H)-dione 8.38 Parts of 2,4-difluoroaniline were added to a solution of 10 parts of cyclohexane-1,2-dicarboxylic anhydride in 100 parts of glacial acetic acid. The mixture was stirred for two hours. The mixture was refluxed for 20 hours and the resulting product was poured into 200 parts of ice. The resulting crystals were filtered and recrystallized twice from 70 parts of methanol at −40° C to yield 10.2 parts of white crystals of 2-(2,4-difluorophenyl)-3a,4,5,6,7,7a-hexahydro-1H-isoindole-1,3(2H)-dione melting at 117°–123° C.

EXAMPLE 4

Preparation of
2-(2,4,6-trifluorophenyl)-3a,4,5,6,7,7a-hexahydro-1H-isoindole-1,3(2H)-dione 9.54 Parts of 2,4,6-trifluoroaniline were added to a solution of 10 parts of cyclohexane-1,2-dicarboxylic anhydride in 100 parts of glacial acetic acid. The mixture was refluxed for 20 hours and the resulting mixture was poured into 200 parts of ice. The resulting crystals were filtered, dried and recrystallized twice from 70 parts of methanol at −40° C to yield 8.3 parts of white crystals of 2-(2,4,6-trifluorophenyl)-3a,4,5,6,7,7a-hexahydro-1H-isoindole-1,3(2H)-dione melting at 129°–131° C.

FORMULATIONS OF THE COMPOUNDS

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few pints to several hundred gallons per acre. High strength compositions are primarily used as intermediates for further formulation. The formulations, broadly, contain about 1% to 99% by weight of active ingredient(s) and at least one of a) about 0.1% to 20% surfactant(s) and b) about 5% to 99% solid or liquid diluent(s). More specifically, they will contain these ingredients in the following approximate proportions:

|  | Percent by Weight | | |
|---|---|---|---|
|  | Active Ingredient | Diluent(s) | Surfactant(s) |
| Wettable Powders | 20–90 | 0–74 | 1–10 |
| Oil Suspensions, Emulsions, Solutions (including Emulsifiable Concentrates) | 5–50 | 40–95 | 0–15 |
| Aqueous Suspensions | 10–50 | 40–84 | 1–20 |
| Dusts | 1–25 | 70–99 | 0–5 |
| Granules and Pellets | 1–95 | 5–99 | 0–15 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers," 2nd. Edn., Dorland Books, Caldwell, N.J. The more absorptive diluents are preferred for wettable powders and the denser ones for dusts. Typical liquid diluents and solvents are described in Marsden, "Solvents Guide," 2nd. Edn., Interscience, New York, 1950. Solubility under 0.1% is preferred for suspension concentrates; solution concentrates are preferably stable against phase separation at 0° C. "McCutcheon's Detergents and Emulsifiers Annual", Allured Publ. Corp., Ridgewood, New Jersey, as well as Sisely and Wood, "Encyclopedia of Surface Active Agents", Chemical Publ. Co., Inc., New York, 1964, list surfactants and recommended uses. All formulations can contain minor amounts of additives to reduce foam, caking, corrosion, microbiological growth, etc. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 4th. Edn., McGraw-Hill, N.Y., 1963, pp. 8-59ff.

For further information regarding the art of formulation, see for example:

H. M. Loux, U.S. Pat. No. 3,235,361, Feb. 15, 1966, Col. 6, Line 16 through Col. 7, Line 19 and Examples 10 through 41.

R. W. Luckenbaugh, U.S. Pat. No. 3,309,192, Mar. 14, 1967, Col. 5 Line 43 through Col. 7 Line 62 and Ex. 8, 12, 15, 39, 41, 52, 53, 58, 132, 138–140, 162–164, 166, 167, 169–182.

H. Gysin and E. Knusli, U.S. Pat. No. 2,891,855, June 23, 1959, Col. 3 Line 66 through Col. 5 Line 17 and Examples 1–4.

G. C. Klingman, "Weed Control as a Science," John Wiley & Sons, Inc., New York, 1961 pp. 81–96.

J. D. Fryer and S. A. Evans, "Weed Control Handbook", 5th Edn. Blackwell Scientific Publications, Oxford, 1968, pp. 101–103.

EXAMPLE 5

Wettable Powder

| | |
|---|---|
| 2-(4-chloro-2-fluorophenyl)-3a,4,5,6,7,7a-hexahydro-1H-isoindole-1,3-(2H)-dione | 40% |
| dioctyl sodium sulfosuccinate | 1.5% |
| sodium ligninsulfonate | 3% |
| low viscosity methyl cellulose | 1.5% |
| attapulgite | 54% |

The ingredients are thoroughly blended, passed through an air mill, to produce an average particle size under 15 microns, reblended, and sifted through a U.S.S. No. 50 sieve (0.3 mm opening) before packaging.

All compounds of the invention may be formulated in the same manner.

EXAMPLE 6

AQUEOUS SUSPENSION

| | |
|---|---|
| 2-(4-chloro-2-fluorophenyl)-3a,4,5,6,7,7a-hexahydro-1H-isoindole-1,3(2H)-dione | 25% |
| hydrated attapulgite | 3% |
| crude calcium ligninsulfonate | 10% |
| sodium dihydrogen phosphate | 0.5% |
| water | 61.5% |

The ingredients are ground together in a ball or roller mill until the solid particles have been reduced to diameters under 10 microns.

EXAMPLE 7

High Strength Concentrate

| | |
|---|---|
| 2-(4-chloro-2-fluorophenyl)-3a,4,5,6,7,7a-hexahydro-1H-isoindole-1,3(2H)-dione | 98.5% |
| silica aerosol | 0.5% |
| synthetic amorphous fine silica | 1.0% |

The ingredients are blended and ground in a hammer mill to produce a high strength concentrate substantially all, e.g., 79.5%, passing a U.S.S. No. 50 sieve (0.3 mm openings). This material may then be formulated in a variety of ways shown in the art.

EXAMPLE 8

Dust

| | |
|---|---|
| high strength concentrate from Example 7 | 25.4% |
| pyrophyllite, powdered | 74.6% |

The materials are thoroughly blended and packaged for use.

EXAMPLE 9

Solution

| | |
|---|---|
| 2-(4-chloro-2-fluorophenyl)-3a,4,5,6,7,7a-hexahydro-1H-isoindole-1,3(2H)-dione | 25.0% |
| dimethyl formamide | 75.0% |

The ingredients are combined and stirred to produce a solution. This can be used for low volume application.

EXAMPLE 10

Granules

The solution of Example 9 is sprayed onto preformed montmorillonoid clay granules (0.6 – 2.5 mm diameter) tumbling in a rotating drum. The rate of spray is adjusted to produce a 5% active granule which is then packaged and is ready for use.

EXAMPLE 11

Oil Suspension

| | |
|---|---|
| 2-(4-chloro-2-fluorophenyl)-3a,4,5,6,7,7a-hexahydro-1H-isoindole-1,3(2H)-dione | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

UTILITY

The compounds of formula I are useful for the selective preemergence weed control of undesired vegetation in crops such as rice, soybeans, peanuts, lima beans, green beans and squash. The compounds of this invention can also be used as directed treatments for the pre/post-emergence control of weeds in various crops including soybeans, peanuts, garden beans and rice. In addition, these compounds are useful wherever general weed control is required, such as industrial sites, railroad and utility rights-of-way, along fences, building foundations, parking and storage lots, etc.

The precise amount of the compounds of formula I to be used in any given situation will vary according to the particular end result desired, the use involved, the plant and soil involved, the formulation used, the mode of application, prevailing weather conditions, foliage density and like factors. Since so many variables play a role, it is not possible to state a rate of application suitable for all situations. Broadly speaking, the compounds of the invention are used at levels of about 0.125 to about 20 kilograms, preferably about 0.25 to about 10, per hectare. The lower rates in this range will generally be selected on lighter soils, soils low in organic matter content, for selective weed control in crops, or in situations where maximum persistence is not necessary.

Herbicidal activity of compounds of this invention was discovered in a greenhouse test.

TEST PROCEDURE

Seeds of crabgrass (Digitaria spp.), barnyardgrass (Echinochloa crusgalli), wild oats (*Avena fatua*), Cassia tora, morningglory (Ipomoea spp.), cocklebur (Xanthium spp.), sorghum, corn, soybean, rice, wheat and nutsedge tubers were planted in a growth medium and treated preemergence with the chemicals dissolved in a non-phytotoxic solvent. At the same time, cotton having five leaves (including cotyledonary ones), bush beans with the third trifoliate leaf expanding, crabgrass with two leaves, barnyardgrass with two leaves, wild oats with one leaf, cassia with three leaves (including cotyledonary ones), morningglory with four leaves (including the cotyledonary ones), cocklebur with four leaves (including the cotyledonary ones), sorghum with three leaves, corn with three leaves, soybean with two cotyledonary leaves, rice with two leaves, wheat with one leaf, and nutsedge with three-five leaves were sprayed. Treated plants and controls were maintained in a greenhouse for sixteen days, then all species were compared to controls and visually rated for response to treatment.

A quantitative rating was made on a scale of 0 to 10; a rating of 10 means complete kill, a rating of 0 means no injury. A quantitative rating for type of injury was also made, the letter "B" denotes foliage burn, "D" indicates defoliation, "C" stands for chlorosis/necrosis are "H" means formulative effects.

| COMPOUND | POST EMERGENCE | | | | | | | | | | | | | | |
|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 |
| 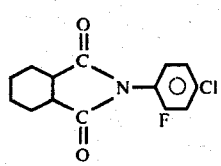 | 2 | | 10B | 7B 7D | 10B | 10B | 10B | 5B | 10B | 10B | 9B | 8B | 7B | 9B | 6B | 9B |

| COMPOUND | PRE-EMERGENCE | | | | | | | | | | | |
|---|---|---|---|---|---|---|---|---|---|---|---|---|
| | 4 | 5 | 6 | 7 | 8 | 9 | 10 | 11 | 12 | 13 | 14 | 15 |
| 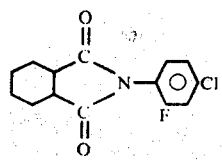 | | 5H | 6H | 4C | 9G | 10C | 10C | 8C | 9C | 8H | 4H | 1C | 9H |

| | | |
|---|---|---|
| 1 = Kg. Ha. | 6 = CASSIA | 11 = WHEAT |
| 2 = Bush Bean | 7 = NUTSEDGE | 12 = CORN |
| 3 = COTTON | 8 = CRABGRASS | 13 = SOYBEAN |
| 4 = MORNING GLORY | 9 = BARNYARD GRASS | 14 = RICE |
| 5 = COCKLEBUR | 10 = WILD OATS | 15 = SORGHUM |

Ratings for one of the compounds tested by this procedure are recorded in the Table.

The data in the Table illustrate that a compound of the instant invention is an extremely effective preemergence herbicide but causes little or no damage to rice as evidenced by the 1C rating. By contrast, crabgrass is destroyed preemergence and so is barnyardgrass. Other weeds such as wild oats are also effectively contained.

What is claimed:
1. A compound of the formula

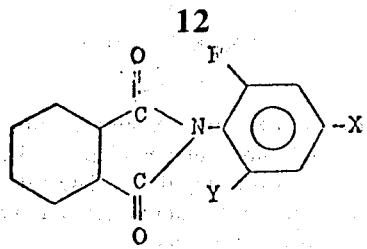

wherein X is Cl, Br or F, and Y is H or F, provided that when Y is F, X is F.

2. A compound of claim 1, 2-(4-chloro-2-fluorophenyl-3a,4,5,6,7,7a-hexahydro-1H-isoindole-1,3a(2H)-dione.

3. A compound of claim 1, 2-(4-bromo-2-fluorophenyl)-3a,4,5,6,7-7a-hexahydro-1H-isoindole-1,3(2H)-dione.

* * * * *